July 5, 1966 D. L. ARMSTRONG ETAL Plant Pat. 2,654
ROSE PLANT
Filed Aug. 17, 1965
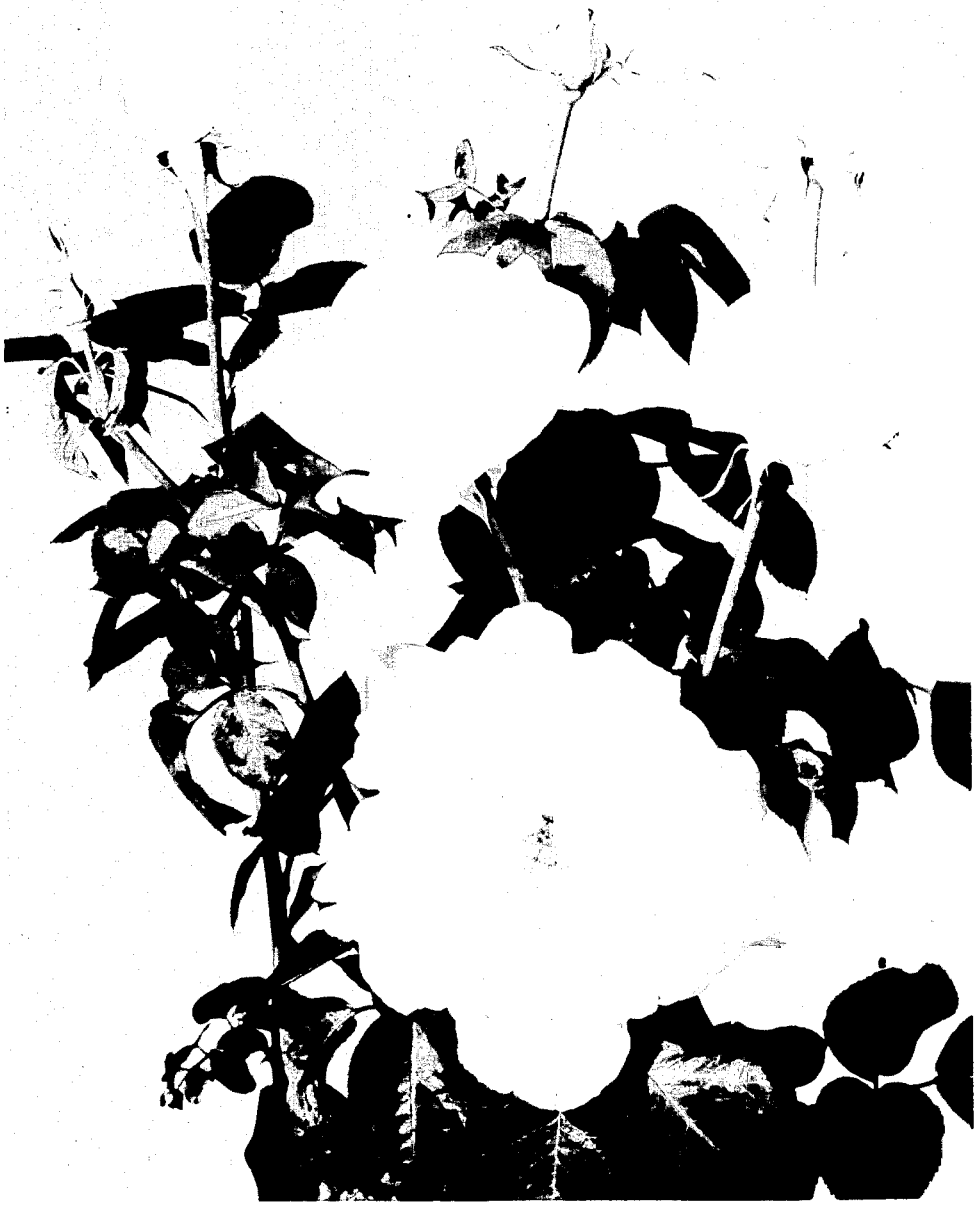
Inventors.
D. L. Armstrong
H. C. Swim
By: Robb & Robb
Attorneys.

United States Patent Office

Plant Pat. 2,654
Patented July 5, 1966

2,654
ROSE PLANT

David L. Armstrong and Herbert C. Swim, both of Ontario, Calif., assignors to Armstrong Nurseries, Inc., Ontario, Calif., a corporation of California Filed Aug. 17, 1965, Ser. No. 480,537
1 Claim. (Cl. Plt.—18)

The present invention relates to a new and distinct variety of rose plant of the hybrid tea class, which was originated by us by crossing an unnamed rose variety which is the subject of Plant Patent No. 1,254, with an unnamed and unpatented seedling of unidentified parentage, the first unnamed variety being the seed parent, and the second unnamed variety being the pollen parent.

The general objective of this breeding was to produce a new and improved hybrid tea rose variety having flowers of the white or near white color range, while combining the vigor, quite double petalage and good hybrid tea habit, with long single stems, of the seed parent, along with the excellent urn-shaped buds, white flower color and good disease resistance for a white flowered rose variety of the pollen parent.

This objective was fully achieved, along with other desirable improvements, as evidenced by the following characteristics which are outstanding in the new variety and which distinguish it from its parents, as well as from all other varieties of which we are aware:

(1) A very vigorous plant habit which is much greater than that of other hybrid tea rose varieties in the near white color range;

(2) Attractive, dark green, glossy and disease resistant foliage;

(3) Excellent, long, urn-shaped buds;

(4) Double flowers of large size which are borne singly on long stems;

(5) A distinctive and attractive general color tonality of the flowers corresponding to pale blush pink, or near white, which contrasts in a very attractive manner with the dark green foliage; and (6) A strong flower fragrance.

In comparison with its seed parent, the flowers of our new variety have considerably less petalage than those of this parent, and the flower color is pale blush pink, or near white, as distinguished from the light yellow flower color of the parent.

As compared with its pollen parent, the new variety is much more vigorous, the flowers are borne on much longer stems and more often on single stems, while the flowers are near white, with a trace of pale pink, while those of this parent have no pale pink coloring at anytime, and the flowers of the new variety have a very strong fragrance, while those of this parent have virtually no fragrance.

Asexual reproduction of our new variety by budding, as performed at Ontario, California, shows that the foregoing characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as (W)) and Robert Ridgway's Color Standards and Nomenclature (hereinafter abbreviated as (R)), as indicated:

Type: Tall; bush; outdoor; seedling; for cut flowers and for garden decoration.
Class: Hybrid tea.
Breeding: Seedling.
*Seed parent.*—An unnamed variety which is the subject of Plant Patent No. 1,254.
*Pollen parent.*—An unnamed seedling of unidentified parentage.
Propagation: Holds its distinguishing characteristics through succeeding propagations by budding.

*Flower*

Locality where grown and observed: Ontario, California.
Flowers borne: Usually singly, but sometimes from 3 to 5 to stem; in irregular clusters; on strong and long stems.
Quantity of bloom: Very free, outdoors.
Continuity: Nearly continuous during growing season.
Fragrance: Strong.
Bud:
*Peduncle.*—From average length to long; from average caliper to heavy; erect; usually smooth; with none to several small stipitate glands and none to few small hairs. Color—near Apple Green, Plate XVII (R).
*Before calyx breaks.*—Size—from medium to large. Form—from medium length to long; ovoid.
*As calyx breaks.*—Color—near Naples Yellow, Plate 403/1, page 121 (W), overlaid with near Fuchsia Purple, Plate 28/1, page 28 (W) on side exposed to the sun.
*Sepals.*—Inner surface—with fine wooly tomentum. Outer surface—usually smooth. Alternate margins—lined with fine wooly tomentum. Other margins—lined with several to many small stipitate glands and with small slender foliaceous parts, some sepals having foliaceous appendages extending from ¼ to ½ of sepal length.
*As first petal opens.*—Size—from average to large. Form—long; ovoid; usually urn-shaped. Color: Outside—between white and Dawn Pink, Plate 523/3, page 137 (W), blending with near Rhodamine Pink, Plate 527/3, page 138 (W) to the base of petal, with small area at base of petal near Sap Green, Plate 62/1, page 62 (W); inside—between white and Rose Pink, Plate 427/3, page 126 (W), with small area at base of petal near Primrose Yellow, Plate 601, page 65 (W).
*Opening.*—Opens up well; is not retarded or prevented from opening by cold, hot, wet or dry weather.
Bloom:
*Size (when fully open).*—Large; from 4½ inches to 5½ inches.
*Petalage.*—Double; from 24 to 35 petals plus 4 to 6 petaloids; arranged irregularly.
*Form.*—High-centered at first, but becoming from cupped to high-centered; petals being at first tightly cupped, with tips reflexed slightly outward, but later becoming more loosely flat to cupped with tips reflexed outward at maturity; outside and intermediate petals of both newly opened and 3-days opened flowers usually reflexed slightly outward both along edges and apex of petals, with outside petals of 3-days opened flower usually strongly reflexed outward.

Petals:

*Texture.*—Thin; moderately leathery and soft.

*Appearance.*—Inside—satiny. Outside—satiny.

*Shape.*—Outside—between round and broadly obovate, with apex flat, and sometimes with one or two notches. Intermediate—obovate, with apex rounded to flat and sometimes with one or two notches. Inside—obovate, with apex rounded and sometimes with one or two notches.

This description of a newly opened flower was made from a rose grown outdoors during the month of September at Ontario, California:

*Color.*—Outer petal: Outside surface—near white, with a slight shading of near Dawn Pink, Plate 523/3, page 137 (W) toward base of petal, with small area at base of petal near Sap Green, Plate 62/2, page 62 (W); inside surface—near white, with small area at base of petal near attachment near Dresden Yellow, Plate 64/1, page 64 (W). Intermediate petal: Outside surface—between white and Dawn Pink, Plate 523/3, page 137 (W), with small area at base of petal near attachment near Sap Green, Plate 62/1, page 62 (W); inside surface—near white, with small area at base of petal near attachment near Dresden Yellow, Plate 64/1, page 64 (W). Inner petal: Outside surface—between white and French Rose, Plate 520/3, page 136 (W), with small area at base of petal near attachment near Dresden Yellow, Plate 64/1, page 64 (W); inside surface—near white, with small area at base of petal near attachment near Primrose Yellow, Plate 601/1, page 65 (W).

This description was made from a rose that was open for three days outdoors during the month of September at Ontario, California:

*Color.*—Outer petal: Outside surface—near white, with small area at base of petal near attachment near Primrose Yellow, Plate 601/2, page 65 (W); inside surface—near white, with small area at base of petal near attachment near Primrose Yellow, Plate 601/2, page 65 (W). Inner petal: Outside surface—near white, with a very slight shading of near Rose Pink, Plate 427/3, page 126 (W); inside surface—near white, with small area at base of petal near Primrose Yellow, Plate 601/3, page 65 (W).

*General color effect.*—Newly opened flower—between white and French Rose, Plate 520/3, page 136 (W). 3-days open—near white, with a very slight shading of near Rose Pink, Plate 427/3, page 126 (W) toward center of flower.

*Behavior.*—Drop off cleanly; not particularly affected by cold, hot, wet or dry weather.

*Flower longevity.*—On bush in garden—4 or 5 days in October. Cut roses grown outdoors and kept at living room temperatures—3 or 4 days in October.

*Reproductive organs*

Stamens: From average number to many; arranged regularly about pistils; a few mixed with petaloids.

Filaments: From medium length to long (from 6 mm. to 15 mm.); most with anthers. Color—near Poppy Red, Plate 16/2, page 16 (W).

Anthers: From medium size to large; all open approximately at once. Color: Upper side—margins near Saffron Yellow, Plate 7/2, page 7 (W), with remainder near Mimosa Yellow, Plate 602/2, page 143 (W); under side—margins near Saffron Yellow, Plate 7/2, page 7 (W), with remainder near Mimosa Yellow, Plate 602/2, page 143 (W).

Pollen: From moderate to abundant. Color—near Cadmium Orange, Plate 8/1, page 8 (W).

Pistils: Average number (approximately 80).

Styles: Moderately even; from short to average length; thin caliper; bunched. Color—upper half of style near Scarlet, Plate 22, page 22 (W), with remainder near Canary Yellow, Plate 2/3, page 2 (W).

Stigma: Color—near Nasturtium Orange, Plate 610/3, page 145 (W).

Ovaries: Usually all enclosed in calyx.

Hips: Average length; between obovoid and globular; smooth; walls thick and fleshy. Color (half mature)—near Mignonette Green, Plate XXXI (R).

Sepals: Falling soon; from medium length to long; straight. Color: Inside—Vetiver Green, Plate XLVII (R); outside—near Light Cress Green, Plate XXXI (R).

Seeds: From few to average number (10 to 25) medium size.

*Plant*

Foliage:

*Leaves.*—Compound of usually 3–7 leaflets; abundant; large; leathery; glossy.

*Leaflets.*—Shape—broadly oval, with apex acute. Base—round. Margin—simply serrate.

*Color.*—Mature: Upper surface—between Forest Green, Plate XVII (R) and Empire Green, Plate XXXII (R); under surface—near Chromium Green, Plate XXXII (R). Young: Upper surface—between Chromium Green, Plate XXXII (R) and Deep Dull Yellow-Green (1) Plate XXXII (R); under surface—near Biscay Green, Plate XVII (R), overlaid with near Indian Red, Plate XXVII (R).

*Rachis (the supporting stem of the compound leaf).*—From average size to heavy. Upper side—smooth; grooved; with few to several small stipitate glands on edges. Under side—smooth; with few stipitate glands and none to few small prickles.

*Stipules.*—Medium length; narrow; with points of medium length turning out at an angle of less than 45°.

*Disease resistance.*—Better than average resistance to mildew as compared with other varieties grown under comparable cultural conditions at Ontario, California.

Growth:

*Habit.*—Upright-spreading; much branched.

*Growth.*—Very vigorous.

*Canes.*—Heavy.

*Main stems.*—Color—near Grayish-Olive, Plate XLVI (R). Large prickles—several; from medium length to long; hooked slightly downward; with narrow base of medium length; color—near Light Drab, Plate XLVI (R). Small prickles—few; color—near Light Drab, Plate XLVI (R). Hairs—none.

*Branches.*—Color—near Biscay Green, Plate XVII (R). Large prickles—from few to several; medium length; hooked slightly downward; with narrow base of medium length; color—near Buffy Citrine, Plate XVI (R). Small prickles—from none to few; color—near Buffy Citrine, Plate XVI (R). Hairs—none.

*New shoots.*—Color—near Buffy Brown, Plate XL (R) overlaid with near Indian Red, Plate XXVII (R) on side exposed to the sun. Large prickles—several; from medium length to long; hooked slightly downward; with narrow base of medium length; color—near Indian Red, Plate XXVII (R). Small prickles—from none to few; color—near Indian Red, Plate XXVII (R). Hairs—none.

We claim:

A new and distinct variety of rose plant of the hybrid tea class, substantially as herein shown and described, characterized particularly as to novelty by the unique combination of a very vigorous plant habit which is much greater than that of other hybrid tea rose varieties in the near white color range, attractive, dark green, glossy and disease resistant foliage, excellent, long, urn-shaped buds, double flowers of large size which are borne singly on long stems, a distinctive and attractive general color tonality of the flowers corresponding to pale blush pink, or near white, which contrasts in a very attractive manner with the dark green foliage, and a strong flower fragrance.

No references cited.

ABRAHAM G. STONE, *Primary Examiner.*

R. E. BAGWILL, *Assistant Examiner.*